US010413599B2

United States Patent
Bruins et al.

(10) Patent No.: US 10,413,599 B2
(45) Date of Patent: Sep. 17, 2019

(54) MEDICAMENT AND METHOD FOR TREATING INNATE IMMUNE RESPONSE DISEASES

(71) Applicant: DSM IP ASSETS B.V., Heerlen (NL)

(72) Inventors: Maaike Johanna Bruins, Delft (NL); Luppo Edens, Delft (NL); Helena Maria Nan, Delft (NL)

(73) Assignee: DSM IP ASSETS B.V., Heerlen (NL)

( * ) Notice: Subject to any disclaimer, the term of this patent is extended or adjusted under 35 U.S.C. 154(b) by 117 days.

(21) Appl. No.: 15/101,630

(22) PCT Filed: Dec. 11, 2014

(86) PCT No.: PCT/EP2014/077355
§ 371 (c)(1),
(2) Date: Jun. 3, 2016

(87) PCT Pub. No.: WO2015/086737
PCT Pub. Date: Jun. 18, 2015

(65) Prior Publication Data
US 2016/0346364 A1    Dec. 1, 2016

(30) Foreign Application Priority Data
Dec. 11, 2013   (EP) .................... 13196580

(51) Int. Cl.
| A61K 38/48 | (2006.01) |
| A23L 5/20 | (2016.01) |
| A23L 29/00 | (2016.01) |
| A21D 8/04 | (2006.01) |
| A61K 9/00 | (2006.01) |
| C12N 9/62 | (2006.01) |
| C12C 5/00 | (2006.01) |

(52) U.S. Cl.
CPC ............ *A61K 38/488* (2013.01); *A21D 8/042* (2013.01); *A23L 5/25* (2016.08); *A23L 29/06* (2016.08); *A61K 9/0053* (2013.01); *A61K 38/482* (2013.01); *C12C 5/004* (2013.01); *C12N 9/62* (2013.01); *C12Y 304/21026* (2013.01); *C12Y 304/23018* (2013.01); *C12Y 304/23019* (2013.01); *A23V 2002/00* (2013.01)

(58) Field of Classification Search
None
See application file for complete search history.

(56) References Cited

U.S. PATENT DOCUMENTS

| 2003/0021774 A1 | 1/2003 | Sjoeholm et al. |
| 2004/0191237 A1 | 9/2004 | Davidson et al. |
| 2005/0249719 A1 | 11/2005 | Shan et al. |
| 2008/0193436 A1 | 8/2008 | Shan et al. |
| 2010/0322912 A1 | 12/2010 | Khosla et al. |

FOREIGN PATENT DOCUMENTS

| EP | 2 409 711 | 1/2012 |
| JP | 2011-120601 | 6/2011 |
| RU | 015575 | 10/2011 |
| WO | WO 95/02044 | 1/1995 |
| WO | WO 2005/027953 | 3/2005 |
| WO | WO 2009/075816 | 6/2009 |
| WO | WO 2012/146717 | 11/2012 |
| WO | WO-2012146717 A1 * | 11/2012 | ................ A23J 3/34 |

OTHER PUBLICATIONS

Sasaki, Hiroshi; et al; "The three-dimensional structure of aspergilloglutamic peptidase from Aspergillus niger" Proceedings of the Japan Academy; 80, 435-438, 2004 (Year: 2004).*
Yabuki, Yutaka; et al; "Identification of a glutamine residue essential for catalytic activity of aspergilloglutamic peptidase by site-directed mutagenesis" Federation of European Biochemical Societies, 569, 161-164, 2004 (Year: 2004).*
Ehren, Jennifer; et al; "A Food-Grade Enzyme Preparation with Modest Gluten Detoxification Properties" PLoS One, 4, e6313, 2009 (Year: 2009).*
International Search Report for PCT/EP2014/077355, dated Feb. 10, 2015, 4 pages.
Written Opinion of the ISA for PCT/EP2014/077355, dated Feb. 10, 2015, 5 pages.
A Notice of Reasons for Rejection dated May 15, 2018 in a corresponding Japanese Patent Application No. P2016-536845 (4 pages), and an English Translation thereof (4 pages).
Yabuki, et al., FEBS Letters 569 (2004), pp. 161-164.
Ehren et al., Plos One, vol. 4, Issue 7 (Jul. 2009), e6313, pp. 1-10.
Stoven et al. "Celiac Disease—Advances in treatment via gluten modification" Clin. Gastroenterol. Hepatol. 10:859-862 (2012) (8 pages).
An Official Action dated Jun. 5, 2018, in a related Russian Patent Application No. 2016128070 (7 pages), and an English translation thereof (5 pages).
Matysiak-Budnik et al; *Limited Efficiency of Prolyl-Endopeptidase in the Detoxification of Gliadin Peptides in Celiac Disease*, Gastroenterology 2005; 129:786-796/.
Official Action, CN Appln 201480067431.8 (dated Mar. 8, 2019).

* cited by examiner

*Primary Examiner* — David W Berke-Schlessel
(74) *Attorney, Agent, or Firm* — Nixon & Vanderhye P.C.

(57) ABSTRACT

This invention relates to a medicament or a dietary supplement comprising the *Aspergillus niger* aspergilloglutamic peptidase that is capable of hydrolyzing plant food allergens, and more particularly, alpha-amylase/trypsin inhibitors, thereby treating diseases due to an innate immune response in humans, and/or allowing to delay the onset of said diseases. The present invention relates to the discovery that the *Aspergillus niger* aspergilloglutamic peptidase is capable of hydrolyzing alpha-amylase/trypsin inhibitors that are present in wheat and related cereals said inhibitors being strong inducers of innate immune response. Furthermore, the present invention relates to a method for hydrolyzing alpha-amylase/trypsin inhibitors comprising incubating a composition for food consumption comprising alpha-amylase/trypsin inhibitors with the *Aspergillus niger* aspergilloglutamic peptidase, wherein the inhibitors are hydrolyzed. It also relates to an enzyme composition comprising the *Aspergillus niger* aspergilloglutamic peptidase and an additional enzyme, and to foodstuff comprising the *Aspergillus niger* aspergilloglutamic peptidase.

12 Claims, 5 Drawing Sheets

MEDICAMENT AND METHOD FOR TREATING INNATE IMMUNE RESPONSE DISEASES

This application is the U.S. national phase of International Application No. PCT/EP2014/077355 filed 11 Dec. 2014, which designated the U.S. and claims priority to EP Patent Application No. 13196580.8 filed 11 Dec. 2013, the entire contents of each of which are hereby incorporated by reference.

BRIEF DESCRIPTION OF THE INVENTION

This invention relates to a medicament or a dietary supplement comprising the *Aspergillus niger* aspergilloglutamic peptidase that is capable of hydrolyzing plant food allergens, and more particularly, alpha-amylase/trypsin inhibitors, thereby treating diseases due to an innate immune response in humans, and/or allowing to delay the onset of said diseases. The present invention relates to the discovery that the *Aspergillus niger* aspergilloglutamic peptidase is capable of hydrolyzing alpha-amylase/trypsin inhibitors that are present in wheat and related cereals said inhibitors being strong inducers of innate immune response. Furthermore, the present invention relates to a method for hydrolyzing alpha-amylase/trypsin inhibitors comprising incubating a composition for food consumption comprising alpha-amylase/trypsin inhibitors with the *Aspergillus niger* aspergilloglutamic peptidase, wherein the inhibitors are hydrolyzed. It also relates to an enzyme composition comprising the *Aspergillus niger* aspergilloglutamic peptidase and an additional enzyme, and to foodstuff comprising the *Aspergillus niger* aspergilloglutamic peptidase.

BACKGROUND OF THE INVENTION

Plant food allergens are a widespread group of plant proteins comprising cupin and prolamin superfamilies as well as proteinaceous molecules of the plant defense system. The prolamin superfamily includes several important types of allergens of legumes, tree nuts, cereals, fruits, and vegetables, and the cereal alpha-amylase and protease inhibitors. Cereal prolamine are major storage proteins of the cereal grain endosperm and are named glutenins and gliadins in wheat, secalins in rye, and hordeins in barley. The proteinaceous alpha-amylase inhibitors are non-gluten proteins. Based on structural similarity, proteinaceous alpha-amylase inhibitors with plant origin are usually classified in six families including lectin-like, knottin-like, CM-proteins. Kunitz-like, c-purothionin-like, and thaumatin-like (Richardson, 1990). CM (Chloroform-methanol)-proteins are a large protein family from cereal seeds containing 120 to 160 amino acid residues and five disulfide bonds. They show a typical double-headed alpha-amylase/trypsin domain. This feature makes it possible that they inhibit the activity of alpha-amylase and trypsin-like enzymes. The alpha-amylase inhibitor 0.19 is one of the most studied inhibitor of this family; it has a broad specificity, and inhibits alpha-amylases from insects, birds and mammals.

Furthermore, plant defensive proteins also comprise protease inhibitors. Most plant storage organs such as seeds and tubers contain 1-10% of their total proteins as protease inhibitors with different biochemical and structural properties inhibiting different types of proteases. Protein inhibitors are classified based on the type of enzyme they inhibit: serine protease inhibitors, cysteine protease inhibitors, aspartic protease inhibitors, or metallocarboxy-protease inhibitors.

WO 2011/137322 recently disclosed that members of the non-gluten alpha-amylase/trypsin inhibitor family contained in wheat and related cereals are strong inducers of innate immune response in human intestine, thereby contributing to diseases like celiac disease. Moreover, alpha-amylase/trypsin inhibitors are also key contributing factors to diseases or conditions like gluten sensitivity, irritable bowel syndrome, inflammatory bowel disease, but also non-intestinal inflammation.

Celiac disease, also known as celiac sprue, gluten-sensitive enteropathy, or gluten intolerance is one of the most frequent food intolerances worldwide, with highest prevalence in Europe, North and South America, and Australia. Celiac disease is an inflammatory disease of the upper small intestine in genetically predisposed persons triggered by the ingestion of wheat, barley, rye and their cross-related varieties leading to a mal-absorption syndrome.

Gluten is a common dietary protein present in wheat, barley, rye and their cross-related varieties. Gluten is a complex mixture of glutamine- and proline-rich glutenin and prolamine molecules, which is thought to be the responsible factor for celiac disease induction in sensitive human individuals. Because of their unusual structure, with a high proline and glutamine content, the gluten proteins are partly resistant to intestinal enzymes, which lead to several non-degraded immunogenic peptides that can be sensed by the intestinal immune system. Ingestion of such proteins by sensitive individuals produces flattening of the normally luxurious, rug-like, epithelial lining of the small intestine known to be responsible for efficient and extensive terminal digestion of peptides and other nutrients. Clinical symptoms of Celiac Sprue include fatigue, chronic diarrhea, malabsorption of nutrients, weight loss, abdominal distension, anemia, as well as a substantially enhanced risk for the development of osteoporosis and intestinal malignancies (lymphoma and carcinoma). The disease has an incidence of approximately 1 in 200 in European and North American populations.

The current essential treatment of gluten intolerance is a permanent strict withdrawal of gluten form the diet which is difficult to maintain. It is however important to define two categories of gluten intolerance in order to understand how the illness is affected by enzyme action in the gut. Celiac sprue is an autoimmune condition, a genetic inflammatory disorder of the small intestine. When gluten proteins break down during digestion, they fragment. These protein fragments are called peptides. In celiac sufferers, an inappropriate immune system response in the small intestine is initiated by one type of peptide, and the intestinal cells are damaged.

A second type of gluten intolerance results when the gut is injured by something other than celiac disease—the negative effect of a bacteria or yeast infection, for example, resulting in the loss of the intestinal enzymes which in turn leads to poor gluten digestion. While supplementing individuals with enzymes may be beneficial to celiac sufferers, they must remain on a strictly gluten free diet because of the possible strength of the autoimmune reaction when traces of gluten are left undigested.

Using specific enzymes as supplement can be effective in minimizing the need for a gluten-free diet for those individuals at risk of developing gluten intolerance, for gluten sensitive individuals, or wherein gluten intolerance is due to gut injury.

The use of exogenous proteolytic enzymes for gluten detoxification has been one of the most promising strategies for celiac disease management. Such enzymes have been used in both pretreatment of gluten containing flours, and as supplements. Prolyl-endopeptidases are known gluten-digesting enzymes which have been shown to digest gliadin peptides (WO 2002/45524 and WO 2002/46381).

WO 2011/137322 disclosed the use of antibodies against alpha-amylase CM 3 in order to treat celiac patients or food compositions, and considers the use of protease as an alternative. However, it is silent with regard to a specific enzyme treatment to efficiently hydrolyze alpha-amylase/trypsin inhibitors in the gastrointestinal tract or in pretreatment of foodstuff derived from wheat barley, rye and their cross-related varieties.

The indolins and purothionins comprise a group of sulphur-rich and basic low molecular weight proteins that are present in the endosperm of several Graminae. For example, the sequence identity of alpha-purothionins from wheat, rye and barley is more than 80%. Purothionin is a member of an allergy family designated by the World Health Organization-International Union of Immunological Societies as "Tri a 37" and might represent a diagnostic marker for an increased risk of wheat-induced anaphylaxis (Pahr et al., J Allergy Cin Immunol., 132 (4), pp 1000-1003).

It would be desirable to provide a safe, effective and cost competitive way to degrade alpha-amylase/trypsin inhibitors in the gastro intestinal tract as well as in food compositions comprising such inhibitors in order to treat celiac disease, enhance gastrointestinal comfort in celiac or non-celiac gluten sensitive individuals, or to delaying the onset of gastrointestinal discomfort in non-celiac gluten sensitive healthy individuals by reducing the exposure of the gut to plant allergens and more specifically to alpha-amylase/trypsin inhibitors such as CM 3 and 0.19. The use according to the present invention not only solves the problem of gluten sensitivity/allergy, but also allows stabilizing foam when used to degrade amylase trypsin inhibitors in beer.

DETAILED DESCRIPTION OF THE INVENTION

Surprisingly, the present inventors have found that an enzyme: the *Aspergillus niger* aspergilloglutamic peptidase has a great potential to hydrolyze plant allergens such as alpha-amylase/trypsin inhibitors in the gastro intestinal system of an individual, as well as in food matrices containing said inhibitors and therefore can be used as medicament, dietary supplement, in food pre-treatment or in a process to prepare a baked product.

The present invention thus relates to a dietary supplement or a pharmaceutical composition comprising the *Aspergillus niger* aspergilloglutamic peptidase, a prolyl-endopeptidase, and pharmaceutically or dietary acceptable excipients. The *Aspergillus niger* aspergilloglutamic peptidase (AGP) formerly called aspergillopepsin II isolated from *Aspergillus niger.* var. *macrosporus* (EC 3.4.23.19) is a unique protease belonging to the peptidase family A4. This enzyme is not homologous to the aspartic proteases belonging to peptidases of family A1. which are typical pepsin-type acid proteases, thus being insensitive to their specific inhibitors such as pepstatin A. Therefore this enzyme was also classified as a 'pepstatin-insensitive' acid proteinase. Among the glutamic peptidases so far known, AGP is characteristic in that it is the sole two-chain enzyme. The amino acid sequence of the enzyme has no homology with those of typical aspartic proteinases.

The term *Aspergillus niger* aspergilloglutamic peptidase according to the present invention includes enzymes having at least 70% identity to the amino acid sequence of the *Aspergillus niger* aspergilloglutamic peptidase (UniProtKB/Swiss-Prot identifier P24665), for instance an enzyme having at least 80, 85, 90, 95, 98, 99% identity to P24665. Most preferred homologous enzymes according to the present invention are scytalidoglutamis peptidase from *Scytalidium lignicolum*, acid peptidases B and C from *Crypphonectria parasitica*, and an acid protease from *Sclerotina sclerotiorum*.

The *Aspergillus niger* aspergilloglutamic peptidase in the dietary supplement or the pharmaceutical composition as disclosed herein may be present in a pure form, or as a preparation comprising the *Aspergillus niger* aspergilloglutamic peptidase, wherein at least 40%, 50%, 60%, 70%, 80%, 90%, 95% or more of the protease activity is derived from the *Aspergillus niger* aspergilloglutamic peptidase, wherein the activity is expressed in HPU (Histidine Protease Units); One HPU is the amount of enzyme that hydrolyzes an amount of haemoglobin per minute, giving a solution with an optical density at 275 nm equal to the optical density of a solution containing 1 μg L-tyrosine per mL in 0.1 mol/L HCl solution. Conditions of the test are: pH 1.75, temperature 40° C., haemoglobin concentration during incubation 16.7 g/L.

Activity (HPU/mL)=$(OD_{sample}-OD_{blank}/S) \times 11/30$

Wherein:
$OD_{sample}$: Optical density of the sample filtrate (275 nm)
$OD_{blank}$: Optical density of the sample blank filtrate (275 nm)
S: OD of a L-tyrosine standard solution of 1.1 μg/mL (mL/μg)
30: incubation time (minutes)
11: total volume reaction mixture (mL).

The *Aspergillus niger* aspergilloglutamic peptidase according to the present invention can be prepared as disclosed in Handbook of Proteolytic Enzymes, A. J. Barret, N. D. Rawlings, and J. F. Woessner eds.; Academic Press; or in PCT/EP2013/066899.

The term "pharmaceutical composition" refers to a medicament or a drug, while the term "dietary supplement" refers to a small amount of an active principle for supplementation of a human diet packaged in single or multidose units. Dietary supplements do not generally provide significant amounts of calories, but may contain other micronutrients like minerals or vitamins.

The dietary supplement or pharmaceutical composition according to the present invention further comprises pharmaceutically acceptable excipients. "Excipients" mean excipients, carriers, or diluents, including, but not limited to, water, gelatin of any origin, vegetable gums, ligninsulfonate, talc, sugars, starch, cellulose, microcrystalline cellulose, gum arabic, vegetable oils, polyalkylene glycols, flavoring agents, preservatives, stabilizers, emulsifying agents, buffers, lubricants, colorants, wetting agents, fillers, and the like. The carrier material can be organic or inorganic inert carrier material suitable for oral/parenteral/injectable administration.

In the present invention, the *Aspergillus niger* aspergilloglutamic peptidase dietary supplement or pharmaceutical composition provides from 1 to 100 HPU units of *Aspergillus niger* aspergilloglutamic peptidase, preferably from 10 to 50 HPU per serving.

Furthermore, the dietary supplement or pharmaceutical composition according to the present invention further comprises a prolyl-endopeptidase. Mammalian prolyl-endopeptidase is a large cytosolic enzyme that belongs to a distinct class of serine peptidases. It was first described in the cytosol of rabbit brain as an oligopeptidase, which degrades the nonapeptide bradykinin at the Pro-Phe bond. The enzyme is involved in the maturation and degradation of peptide hormones and neuropeptides such as alpha-melanocyte-stimulating hormone, luteinizing hormone-releasing hormone (LH-RH), thyrotropin-releasing hormone, angiotensin, neurotensin, oxytocin, substance P and vasopressin. A prolyl-oligopeptidase cleaves peptide bonds at the C-terminal side of proline residues. Its activity is confined to action on oligopeptides of less than 10 kD and it has an absolute requirement for the trans-configuration of the peptide bond preceding proline.

Most preferred prolyl-endopeptidase according to the present invention is the fungal *Aspergillus niger* prolyl-endopeptidase enzyme (AN-PEP). AN-PEP can be sourced from DSM Food Specialties (Delft, The Netherlands). Combination of both AN-PEP and AGP allows addressing in a single dietary supplement or pharmaceutical composition both aspects of gluten intolerance/sensitivity by providing enzymes for hydrolysis of both alpha-amylase/trypsin inhibitors and gluten epitopes in the gastrointestinal tract. In such a case, the dietary supplement or pharmaceutical composition provides from 10,000 to 100,000 Protease Picomole International of prolyl-endopeptidase enzyme. Proline Protease Unit (PPU) is defined as the amount of enzyme that releases 1 μmol of p-nitroanilide per minute at 37° C. in a citrate/disodium phosphate buffer (pH 4.6) using 0.37 mM Z-Gly-Pro-pNA (Bachem, Bubendorf, Switzerland) as substrate.

The dietary supplement or pharmaceutical composition according to the present invention may also further comprise an aspergillopepsin I. Aspergillopepsin I (EC 3.4.23.18) also called *Aspergillus* acid protease, catalyses the hydrolysis of proteins with broad specificity. It generally favors hydrophobic residues in P1 and P1', but also accepts Lys in P1, which leads to activation of trypsinogen. Suitable aspergillopepsin I for all the embodiments of the present invention may be isolated from *Aspergillus niger, Aspergillus saitoi* and *Trichoderma reesei*. Preferably the aspergillopepsin I according to the present invention is isolated form *Aspergillus niger*. In such a case, the dietary supplement or pharmaceutical composition provides from 1 to 1000 HPU units of aspergillopepsin I enzyme, more preferably, from 1 to 100 HPU units per serving.

The dietary supplement or pharmaceutical composition according to the present invention may be in any galenic form that is suitable for administering to humans, but solid or liquid oral forms are preferred, e.g. in solid form, such as additives/supplements for food, tablets, pills, granules, dragées, capsules, gummy formulations, and effervescent formulations such as powders and tablets. The dietary and pharmaceutical compositions may be in the form of controlled (delayed) release formulations.

In all the embodiments of the present invention, the dietary supplement or pharmaceutical composition according to the present invention is preferably in the form of a tablet, a capsule, a sachet, or any other dosage form including liquid formulation. More preferably, it is in the form of a tablet or a capsule. The capsules, tablets or sachets or other dosage forms may be in a container which may take any conventional form. For example the dosage forms may be sold in a jar, bottle, tin box, pot, dispenser, sachet or the like which contains the dosage forms in a predetermined quantity, such as a 30-day supply, a 60-day supply, a 90-day supply or in whatever quantity which is desired. Additionally and optionally, the capsules may be in a blister pack, wherein each blister contains a predetermined number of capsules, usually a single dose (typically 1-4 capsules). The arrangement of the number of capsules in a blister, the number of blisters on a single blister pack strip, and the number of blister pack strips which are sold in a group may be any convenient amounts or configurations.

The dietary or pharmaceutical compositions according to the present invention may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, gelling agents, gel forming agents, antioxidants and antimicrobials.

In the context of the present invention, a pharmaceutical composition is sold with or without a prescription, while a dietary supplement is to be sold over the counter without medical prescription and is to be considered as food.

In another embodiment, the present invention also relates to a dietary supplement or a pharmaceutical composition comprising the *Aspergillus niger* aspergilloglutamic peptidase for use as a medicament. Thus the present invention relates to the use of a dietary supplement or a pharmaceutical composition comprising the *Aspergillus niger* aspergilloglutamic peptidase as a medicament for the treatment of diseases. Preferably, the medicament is for the treatment of a patient suffering from innate immune response in the intestine. Even more preferably, the medicament is for the treatment of celiac disease, non-celiac gluten intolerance, gluten sensitivity, irritable bowel syndrome, or inflammatory bowel disease. Most preferably, the medicament is a dietary supplement for maintaining or enhancing gastrointestinal comfort in gluten sensitive individuals, or for delaying the onset of gastrointestinal discomfort in celiac or non-celiac gluten sensitive individuals, as well as for decreasing alpha-amylase/trypsin inhibitor exposure in healthy individuals, thereby supporting digestion. Alpha-amylase/trypsin inhibitors which are degraded by the present composition are the plant allergens: CM 2, CM 3, CM 16, and 0.19, more preferably CM 3 and 0.19, on the basis of their rapid degradation by the *Aspergillus niger* aspergilloglutamic peptidase. CM 3 amino acid sequence identifier is SwissProt P01083, while 0.19 amino acid sequence identifier is Swiss Prot P01085.

The medicament or dietary supplement according to the present invention is for use by individuals who are desirous to reduce their risk to develop food allergies to plant protein and experiencing gastrointestinal discomfort correlated to celiac sprue, as well as non celiac gluten intolerance.

In a preferred embodiment the medicament is administered orally within 1 hour prior or after ingestion of a meal.

"Gastrointestinal comfort"—is central to the quality of life. Promoting gastrointestinal digestive comfort includes regulating transit time through the gastrointestinal tract and easing the pain associated with digestion and associated disorders.

"Non-celiac gluten sensitive"—Non-celiac gluten sensitivity has been coined to describe those individuals who cannot tolerate gluten and experience symptoms similar to those with celiac disease but yet who lack the same antibodies and intestinal damage as seen in celiac disease. Non-celiac gluten sensitivity is another form of gluten intolerance where the immune response is less characterized. Non-celiac gluten sensitivity shares many symptoms with celiac disease. However, according to Sapone et al. (2012), individuals with non-celiac gluten sensitivity have a prevalence of extra intestinal or non-gastrointestinal symptoms, such as headache, "foggy mind," joint pain, and numbness in the legs, arms or fingers. Symptoms typically appear hours or days after gluten has been ingested, a response typical for innate immune conditions like non-celiac gluten sensitivity.

"Healthy individual"—when used in context of this invention, the healthy individual has not been diagnosed as having a celiac disease.

"Delaying the onset" is meant to include amelioration of the condition, lessening of the severity of the symptoms, early intervention, and lengthening the duration of time prior to the onset of the disease, and is not intended to be limited to a situation where the patient is unable to experience any symptoms of gastrointestinal discomfort.

For the use according to the present invention, the medicament or dietary supplement is administered orally within 1 hour prior or after a meal.

In another embodiment, the present invention relates to a method for degrading plant allergens in a food composition comprising, incubating a food composition containing plant allergens with the *Aspergillus niger* aspergilloglutamic peptidase, for a time sufficient to hydrolyze plant allergens. The person skilled in the art will estimate the amount of enzyme to be added to the food, and the time required to degrade the food allergens depending on the food composition being treated. Detection of food allergens can efficiently be performed by the use of specific antibodies or by mass spectrometry according to methods known in the art. For beer matrices, *Aspergillus niger* aspergilloglutamic peptidase is added at 50 to 2000 HPU/hectoliter of beer, preferably 100 to 1000 HPU/hl beer. For baking composition matrices. *Aspergillus niger* aspergilloglutamic peptidase may be added at 10 to 5000 HPU/Kg of composition. Suitable baking compositions matrices include without limitation a baking composition.

Surprisingly, when using the aspergilloglutamic peptidase in beer processing at low concentration comprised between 0.5 and 500 mg/hl, preferably between 1 and 50 mg/hl, more preferably between 10 to 20 mg/hl, a stabilization of the beer foam occurs.

The plant allergens degraded by the *Aspergillus niger* aspergilloglutamic peptidase are preferably those specifically found in wheat, barley, rye, oat and their cross-related varieties, such as alpha-amylase/trypsin inhibitors, more preferably, the plant allergens are CM 2, CM 3, CM 16, and 0.19, and even more preferably CM 3 and 0.19, on the basis of their rapid degradation by the *Aspergillus niger* aspergilloglutamic peptidase. CM 3 amino acid sequence identifier is SwissProt P01083, while 0.19 amino acid sequence identifier is Swiss Prot P01085.

In the present embodiment the food composition is a food comprising wheat, barley, rye, oat and/or their cross-related varieties. Preferred food compositions are beer, the various process stages involved in beer production, a baking composition, a dough, a sour dough or a baked product such as bread.

In the present method, the *Aspergillus niger* aspergilloglutamic peptidase, may advantageously be complemented with a prolyl-endopeptidase, preferably, the *Aspergillus niger* prolyl-endopeptidase so as to also degrade gluten epitopes, and optionally also with an aspergillopepsin I enzyme.

Preferred amount of enzyme to be added to the food composition in the above method is dependent on the food matrix and the estimated amount of gluten and alpha-amylase/trypsin inhibitor.

In yet another embodiment, the present invention relates to a foodstuff prepared by the method above for degrading plant allergens in a food product comprising, incubating a food composition containing plant allergens with *Aspergillus niger* aspergilloglutamic peptidase, for a time sufficient to hydrolyze plant allergens, said food composition comprising degraded alpha-amylase/trypsin inhibitors. Preferred food is a baked product such as bread, a dough, a beer.

In another embodiment, the present invention also relates to a baking composition, and enzyme composition or a dough comprising the *Aspergillus niger* aspergilloglutamic peptidase. It further relates to a method to prepare a dough comprising the step of adding an *Aspergillus niger* aspergilloglutamic peptidase to at least one dough ingredient.

Baked products are often made using gluten containing flours. Baked products therefore present a food product that could be relevant for gluten sensitive individuals. The baking composition according to the invention comprises wheat, barley, rye, oat and/or their cross-related varieties, preferably in the form of flour and the *Aspergillus niger* aspergilloglutamic peptidase. The baking composition may comprise 10 to 5000 HPU *Aspergillus niger* aspergilloglutamic peptidase/kg of flour.

In an aspect the baking composition comprises the *Aspergillus niger* aspergilloglutamic peptidase in an amount of 20 to 3000 HPU/kg of flour, in an aspect in an amount of 30 to 1000 HPU/kg of flour, in an amount of 40 to 500 HPU/kg of flour, in an amount of 50 to 250 HPU/kg of flour. In an aspect the baking composition comprises 1 ppm-2000 ppm *Aspergillus niger* aspergilloglutamic peptidase having an activity in a range of about 1000 to 50000 HPU/g.

In an aspect the baking composition comprises 10-200 ppm *Aspergillus niger* aspergilloglutamic peptidase having an activity in a range of about 1000 to 50000 HPU/g.

The baking composition according to the invention may comprise at least one additional enzyme as described herein.

"Additional enzyme"—The term additional enzyme herein and herein after includes without limitation an amylase such as an alpha-amylase, beta-amylase, a maltogenic amylase; a cyclodextrin glucanotransferase; a protease, a peptidase such as a prolyl-endopeptidase preferably, the *Aspergillus niger* prolyl-endopeptidase so as to also degrade gluten epitopes, and optionally also with an aspergillopepsin I enzyme; a transglutaminase; a lipase such as a triacyl glycerol lipase, a galactolipase, a phospholipase; cellulose; hemicellulase, in particular a pentosanase such as xylanase; protein disulfide isomerase, e.g. a protein disulfide isomerase as disclosed in WO 95/00636; glycosyltransferase, peroxidase; laccase; or oxidase such as a hexose oxidase, a glucose oxidase, aldose oxidase, pyranose oxidase, lipoxygenase or L-amino acid oxidase; or a G4 forming amylase.

In an embodiment of the enzyme composition according to the invention the additional enzyme is a lipolytic enzyme, preferably a phospholipase, a galactolipase or an enzyme having both phospholipase and galactolipase activity.

In an embodiment of the enzyme composition according to the invention the additional enzyme is Panamore® form DSM as described in WO2009/106575. A suitable lypolitic enzyme may include Lipopan® F, Lipopan® 50 and Lipopan® from Novozymes.

In an embodiment of the enzyme composition of the invention the additional enzyme is an enzyme as described in WO9826057, or as described in U.S. RE38,507, or as described in WO 9943794, in particular in EP1058724B1.

In an aspect of the enzyme composition according to the invention the additional enzyme is an amylase as described in U.S. Pat. No. 8,426,182.

The additional enzyme may include a G4-forming amylase. A G4-forming amylase is an enzyme that is inter alia capable of catalysing the degradation of starch. In particular it is capable of cleaving α-D-(I→4) O-glycosidic linkages in starch. It may be referred to as a glucan 1,4-alpha-maltotetraohydrolase (EC 3.2.1.60). It may also be referred as a maltotetraohydrolase. Suitable G4-forming amylases may be G4-forming amylases described in any one of WO9950399, WO2005007818, WO2004111217, WO2005003339, WO2005007818, WO2005007867, WO2006003461, WO2007007053, WO2007148224, WO2009083592, WO2009088465.

An example of a food product is a baked product.

"Baked product"—The term baked product refers to a baked food product prepared from a dough. Examples of baked products, whether of a white, brown or whole-meal type, which may be advantageously produced by the present invention include bread (in particular white, whole-meal or rye bread), typically in the form of loaves or rolls, French baguette-type bread, pastries, croissants, brioche, panettone, pasta, noodles (boiled or (stir-)fried), pita bread and other flat breads, tortillas, tacos, cakes, pancakes, cookies in particular biscuits, doughnuts, including yeasted doughnuts, bagels, pie crusts, steamed bread, crisp bread, brownies, sheet cakes, snack foods (e.g., pretzels, tortilla chips, fabricated snacks, fabricated potato crisps). The term baked product includes, bread containing from 2 to 30 wt % sugar, fruit containing bread, breakfast cereals, cereal bars, eggless cake, soft rolls and gluten-free bread. Gluten free bread herein and herein after is bread than contains at most 20 ppm gluten. Several grains and starch sources are considered acceptable for a gluten-free diet. Frequently used sources are potatoes, rice and tapioca (derived from cassava) Baked product includes without limitation tin bread, loaves of bread, twists, buns, such as hamburger buns or steamed buns, chapati, rusk, dried steam bun slice, bread crumb, matzos, focaccia, melba toast, zwieback, croutons, soft pretzels, soft and hard bread, bread sticks, yeast leavened and chemically-leavened bread, laminated dough products such as Danish pastry, croissants or puff pastry products, muffins, danish, bagels, confectionery coatings, crackers, wafers, pizza crusts, tortillas, pasta products, crepes, waffles, parbaked products and refrigerated and frozen dough products. Cake herein includes without limitations shortened cake, such as for example pound cake and butter cake, and including foam cakes, such as for example meringues, sponge cake, biscuit cake, roulade, genoise and chiffon cake.

An example of a parbaked product includes, without limitation, partially baked bread that is completed at point of sale or consumption with a short second baking process. The bread may be white or brown pan bread; such bread may for example be manufactured using a so called American style Sponge and Dough method or an American style Direct method.

"Dough"—The term dough is defined herein as a mixture of flour and other ingredients, in particular dough ingredients. In one aspect the dough is firm enough to knead or roll. The dough may be fresh, frozen, prepared or parbaked. The preparation of frozen dough is described by Kulp and Lorenz in Frozen and Refrigerated Doughs and Batters. The term dough herein includes a batter. A batter is a semi-liquid mixture, being thin enough to drop or pour from a spoon, of one or more flours combined with liquids such as water, milk or eggs used to prepare various foods, including cake.

"Dough ingredient"—A dough ingredient includes any component selected from flour, egg, water, salt, sugar, flavours, fat (including butter, margarine, oil and shortening), baker's yeast, a chemical leavening system, milk, oxidants (including ascorbic acid, bromate and Azodicarbonamide (ADA)), reducing agents (including L-cysteine), emulsifiers (including mono/di glycerides, mono glycerides such as glycerol monostearate (GMS), sodium stearoyl lactylate (SSL), calcium stearoyl lactylate (CSL), polyglycerol esters of fatty acids (PGE) and diacetyl tartaric acid esters of mono- and diglycerides (DATEM), gums (including guargum and xanthangum), acids (including citric acid, propionic acid), starch, modified starch, gluten, humectants (including glycerol) and preservatives.

In a preferred embodiment, the present invention relates to an enzyme composition comprising the *Aspergillus niger* aspergilloglutamic peptidase and at least one additional enzyme. The enzyme composition may comprise 10 to 5000 HPU *Aspergillus niger* aspergilloglutamic peptidase/kg of composition.

In an aspect the enzyme composition comprises 1 ppm-2000 ppm *Aspergillus niger* aspergilloglutamic peptidase having an activity in a range of about 1000 to 50000 HPU/g.

In an aspect the enzyme composition comprises 10-200 ppm *Aspergillus niger* aspergilloglutamic peptidase having an activity in a range of about 1000 to 50000 HPU/g.

In an embodiment the enzyme composition according to the invention is provided in a dry form, to allow easy addition to the dough or the at least one dough ingredient, but liquid forms are also possible.

The method according to the invention to prepare a dough comprises the step of adding an *Aspergillus niger* aspergilloglutamic peptidase to at least one dough ingredient. The *Aspergillus niger* aspergilloglutamic peptidase may be added in any step of the dough preparation and may be added in one, two or more steps.

If one or more additional enzymes are to be these enzymes may be added separately or together with the *Aspergillus niger* aspergilloglutamic peptidase according to the invention, for example as the enzyme composition according to the invention, The invention further relates to a process for the production of a baked product, which method comprises baking the dough according to the invention. In an embodiment of the process for the production of baked product the baked product is bread or cake.

The person skilled in the art knows how to prepare a dough or a baked product starting from dough ingredients. The invention further relates to a baked product obtainable by the process for the production of a baked product according to the invention.

The invention relates further to the use an *Aspergillus niger* aspergilloglutamic peptidase in the production of a baked product.

FIGURE LEGENDS

Molecular weight markers: lanes 1, 2, and 15
*A. niger* proline-specific endoprotease treatment at: t=0, lane 3; t=90 minutes, lane 4
*A. niger* aspergilloglutamic peptidase at: t=0, lane 5; t=90 minutes, lane 6
Pepsin at: t=0, lane 7; t=90 minutes, lane 8
Papain at: t=0, lane 9; t=90 minutes, lane 10
Multifect PR 15 L at: t=0, lane 11; t=90 minutes, lane 12
Aspergillopepsin I at: t=0, lane 13; t=90 minutes, lane 14
Pepsin at: t=0, lane 16; t=90 minutes lane 17.

Molecular weight markers (Mark 12™ Unstained Standard, Life Technologies): lane 13.
Purified alpha amylase/protease inhibitors: lane 14.
Without addition of *A. niger* aspergilloglutamic peptidase: lane 1=0, lane 2=60 minutes
0.09 mg/ml *A. niger* aspergilloglutamic peptidase added: lane 3=0, lane 4=60 minutes
0.19 mg/ml *A. niger* aspergilloglutamic peptidase added: lane 5=0, lane 6=60 minutes
0.28 mg/ml *A. niger* aspergilloglutamic peptidase added: lane 7=0, lane 8=60 minutes
0.37 mg/ml *A. niger* aspergilloglutamic peptidase added: lane 9=0, lane 10=60 minutes
0.47 mg/ml *A. niger* aspergilloglutamic peptidase added: lane 11=0, lane 12=60 minutes

Molecular weight markers: lanes 1, 2, 9 and 10
*A. niger* aspergilloglutamic peptidase at: t=0, lane 3; t=90 minutes, lane 4
*A. niger* proline-specific endoprotease at: t=0, lane 5; t=90 minutes, lane 6
Multifect PR 15 L (aspergillopepsin I-like protease from *Trichoderma reesei*) at: t=0, lane 7; and t=90 minutes, lane 8.

Molecular weight markers: lane 1
Purified wheat purothionins: lane 2
Multifect PR 15 L (aspergillopepsin I-like protease from *Trichoderma reesei*; http//biosciences.dupont.com) at: t=0, lane 3; t=90 minutes, lane 4
Mixture of 90% (w/w enzyme protein present) Multifect PR 15 L and 10% *A. niger* aspergilloglutamic peptidase at: t=0, lane 5; t=90 minutes, lane 6

Proctase (non-GMO mixture of proteases secreted by *A. niger* incorporating approx 85% of aspergillopepsin I) at: t=0, lane 7; t=90 minutes, lane 8.

The invention is further illustrated by the following examples.

EXAMPLES

Example 1: *Aspergillus niger* Aspergilloglutamic Peptidase Efficiently Cleaves Wheat Derived Alpha Amylase/Trypsin Inhibitors Under Simulated Stomach Conditions, while Other Acidic Endoproteases are not Efficient Materials & Methods
Production of Aspergillopepsin I from *Aspergillus niger*

The gene for aspergillopepsin I from *Aspergillus niger* (pepA; An14g04710) was over-expressed in an *A. niger* host using methods such as described in WO 98/46772. WO 98/46772 discloses how to select for transformants on agar plates containing acetamide, and to select targeted multicopy integrants. *A. niger* transformants containing multiple copies of the expression cassette were selected for further generation of sample material. The transformed *A. niger* strain was fermented in a modified CSM-fermentation medium, pH 6.2 (40 g/l Maltose, 30 g/l Bacto-soytone, 70 g/l Sodium citrate tribasic dihydrate, 15 g/l $(NH_4)_2SO_4$, 1 g/l $NaH_2PO_4*2H_2O$, 1 g/l $MgSO_4*7H_2O$, 1 g/l L-Arg, 0.25 ml/l Clerol Antifoam). The culture broth obtained was filtered, sterile filtered and than concentrated by ultrafiltration. Chromatography was carried out by applying the enzyme to a Q-sepharose XK 26/10 column in 50 mmol/l Na-acetate, pH 5.6, followed by elution with a salt gradient. The presence of the aspergillopepsin I protein in the various fractions was quantified by judging the intensity of coloured protein bands after 4-12% SDS-PAGE (NuPAGE Bis-Tris Gel, Invitrogen).

Enzymatic Assay

Incubations were carried out in 50 mmol/l Na citrate at pH 4.0 for 90 minutes at 37° C. In all relevant incubations pepsin was present in an enzyme protein concentration of 0.2 mg/ml. The proline-specific endoproteinase was tested in a concentration of 0.5 mg enzyme protein/ml, the other acid endoproteinases in a concentration of 0.05 mg enzyme protein/ml. The amylase inhibitor was added last and present in a concentration of 2 mg/ml.

At t=0, 100 microliter of the reaction mixture was transferred into 400 microliter 25% TCA. After 90 minutes of incubation at 37° C., another 100 microliter was transferred into 400 microliter of fresh TCA solution. After 2 hours at 4° C., the samples were centrifuged for 10 minutes at 14,000 rpm. After centrifugation, 65 microliter of phosphate buffer pH 7, 25 microliter of lithium dodecyl sulfate (LiDS) and 10 microliter of sample reducing agent were added. The samples were stored at 4° C. overnight and than prepared for SDS-PAGE following the Invitrogen protocol (Invitrogen, www.lifetechnologies.com)

Determination of *A. Niger* Aspergilloglutamic Peptidase Activity (HPU)

20.0 g haemoglobin from bovine blood (Sigma product H2625) was suspended in approximately 700 mL water by stirring for 10 minutes at room temperature. After the addition of 3.73 g potassium chloride (KCl) the pH was adjusted to 1.75 with 0.5 mol/L hydrochloric acid. The volume of the haemoglobin suspension was adjusted to 1 L with water. The pH was checked again and adjusted to pH 1.75.

Enzyme solutions were prepared by dissolving purified aspergilloglutamic peptidase produced as disclosed above in a KCl/HCl buffer containing 3.73 g/l KCl adjusted to pH 1.75 with 2.0 mol/L HCl. To test aspergilloglutamic peptidase activity, 5 ml of the haemoglobin solution was heated at 40° C. and subsequently 1 mL enzyme solution with an activity between 5 and 25 Histidine Protease Units (HPU/mL) was added to start the reaction. After 30 minutes the reaction was stopped by adding 5 mL trichloro acetic acid solution (140 g/L) to precipitate larger peptide fragments. A blank measurement was done by adding 1.0 mL enzyme sample to a mixture of 5 mL haemoglobin solution and 5 mL trichloro acetic acid solution. The tubes were incubated at 40° C. for 30 minutes to complete the precipitation. After centrifugation, the optical density of the clear supernatant containing small peptides was measured at 275 nm. The result was compared to an L-tyrosine solution of 1 μg/mL.

One HPU is the amount of enzyme that hydrolyzes an amount of haemoglobin per minute, giving a solution with an optical density at 275 nm equal to the optical density of a solution containing 1 μg L-tyrosine per mL in 0.1 mol/L HCl solution. Conditions of the test are: pH 1.75, temperature 40° C., haemoglobin concentration during incubation 16.7 g/L.

$$\text{Activity (HPU/mL)}=(OD_{sample}-OD_{blank}/S) \times 11/30$$

Where:
$OD_{sample}$: Optical density of the sample filtrate (275 nm)
$OD_{blank}$: Optical density of the sample blank filtrate (275 nm)
S: OD of a L-tyrosine standard solution of 1.1 μg/mL (mL/μg)
30: incubation time (minutes)
11: total volume reaction mixture (mL)

LC-MS/MS Analysis
In-Vitro Digestion

The sample was dissolved to 1 mg/ml in MilliQ water. The solution was 10× diluted in 100 mM NH$_4$HCO$_3$ (pH7.8). The sample was reduced by addition of DTT, 5 mM, 30 minute incubation at room temperature and alkylated by addition of iodoacetamide (IAA), 5.5 mM, 30 minute incubation at room temperature in the dark. Digestion with trypsin was performed at 37° C. overnight.

In Gel Digestion

Gel bands were cut out of the gel using the ExQuest spot cutter (Biorad, Hercules, Calif., USA) and transferred into a lo-protein bind MTP (Eppendorf, Hamburg Germany). The gel pieces were washed by adding 75 μl 50 mM NH$_4$HCO$_3$ to swell and 75 μl Acetronitrile to shrink, total 3 washes. The washed gel pieces were digested with trypsin digestion was performed by incubation at 37° C. overnight. The samples were sonicated for 1 minute and the supernatant was collected into an injection-vial.

LC-MS/MS Analysis

The samples were acidified to 1% formic acid and analyzed on the Accela-LTQ-Velos (Thermo Scientific, San Diego, Calif., USA). The chromatographic separation was achieved with a 2.1×100 mm 1.8 micrometer particle size, 80 Å pore size, C-18 Eclipse)(DB Zorbax column (Agilent Santa Clara, Calif., USA), using a gradient elution with (A) LC-MS grade water containing 0.1% formic acid B) LC-MS grade acetonitrile containing 0.1% formic acid solution (Biosolve BV, the Netherlands) as mobile phases. The gradient was from 5 to 40% B in 83 minutes. The flow rate was kept at 0.4 ml/min, using an injection volume of 25 μl and the column temperature was set to 50° C. MS data acquisition was performed using atop 10 data-dependent acquisition with mass range 400-2000 m/z, using Dynamic exclusion and including charge states 2 and 3 only. MS/MS experiments were performed with an isolation width set at 3.0, and the normalized collision energy was set to 35. Database searches were performed using the Sorcerer 2 (Sorcerer™-SEQUEST®) search engine and the Trans Proteome Pipeline (TPP), using trypsin as preferred enzyme. Only proteins identified with a confidence >90% were considered. The data was searched against the Swissprot database.

Results

Figure 1:
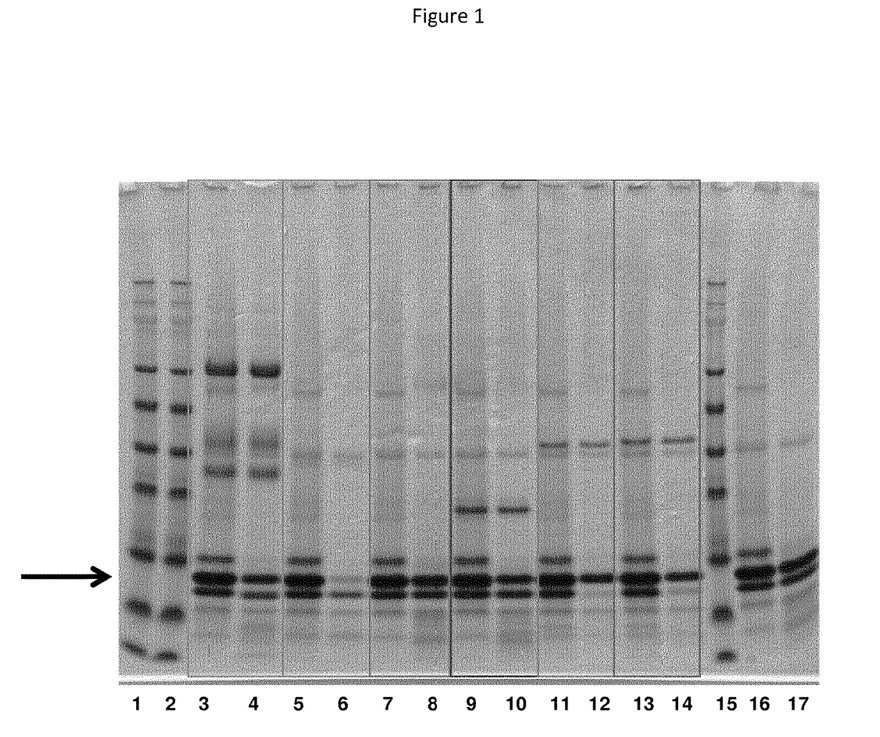
FIG. 1: 4-12% SDS-PAGE (4 to 12% Bis-Tris gel) analysis of various incubations of wheat alpha amylase inhibitors with different proteases plus pepsin under simulated stomach conditions. Two controls with pepsin treatment without additional enzyme are included. The arrow indicates the position of the three major protein products present in the alpha amylase preparation.

In the present Example we demonstrate (See FIG. 1) that, under simulated gastric conditions, only *Aspergillus niger* aspergilloglutamic peptidase among a number of acidic endoproteinases is capable to efficiently degrade a purified preparation incorporating various wheat alpha amylase inhibitors (alpha amylase inhibitor from wheat seed, Type 1, Sigma). In the experiment the efficacies of the following enzymes were compared in the presence of pepsin (control):

pepsin (porcine gastric mucosa, Sigma),
proline-specific endoproteinase from *Aspergillus niger* (MaxiPro PSP, DSM Food Specialities, Delft, The Netherlands)
papain (Collupuline, DSM Food Specialities, Delft, The Netherlands),
*Aspergillus niger* aspergilloglutamic peptidase also called aspergillopepsin II (MaxiPro HSP, DSM Food Specialities, Delft, The Netherlands),
aspergillopepsin I (see Materials & Methods),
Multifect PR 15 L (aspergillopepsin I-like protease from *Trichoderma reesei*; http//biosciences.dupont.com).

The results (cf. FIG. 1), show that the purified wheat gluten alpha amylase inhibitor preparation incorporates three major protein bands with a size of approximately 12 kDa (see arrow). These data also show that under simulated stomach conditions and in the presence of pepsin and equal amounts of the various proteinases, the *Aspergillus niger* aspergilloglutamic peptidase is most effective in degrading these three major bands present in a purified preparation of alpha amylase inhibitors.

To confirm the nature of the different proteins present in each one of these bands, samples of gel bands were cut out, extracted and the proteins present were identified using LC-MS/MS analysis as described in the Materials & Methods above.

Figure 2:
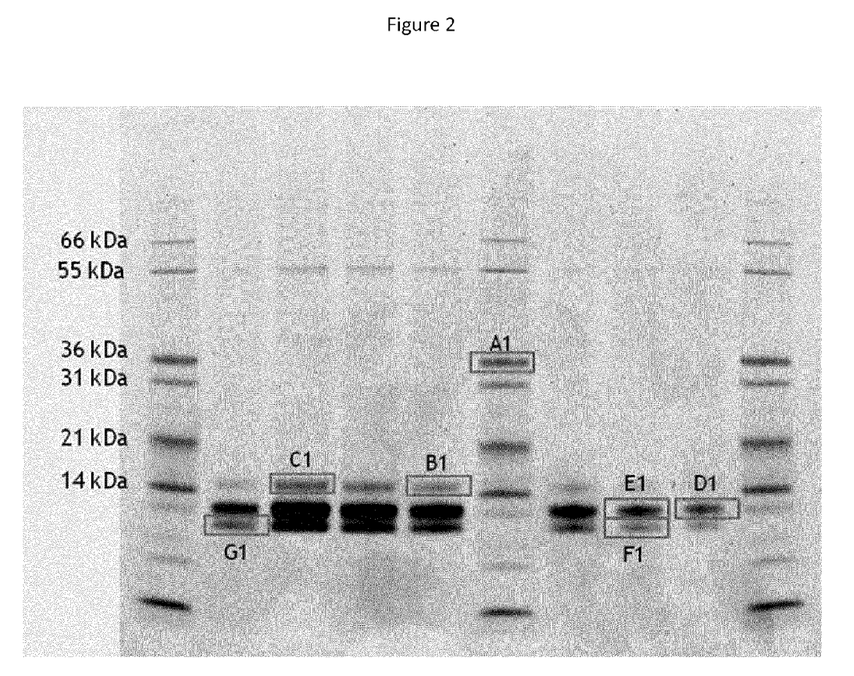
FIG. 2: Preparative SDS-PAGE of wheat alpha amylase inhibitors to identify the nature of the most abundant proteins present in bands B1 to G1.

In this case the 10 mg/ml of the Sigma alpha amylase inhibitor solution was diluted 10 times with water. Than 65 microliter of this solution was mixed with 25 microliter of LiDS sample buffer and 10 microliter of the sample reducing agent, heated for 10 minutes at 70° C. after which the proteins were separated by SDS-PAGE according to the Invitrogen protocol. Then the gel was fixed for 1 hour with 50% methanol/7% acetic acid, rinsed twice with demineralized water and stained with Sypro Ruby overnight. Gel samples were obtained of the three, presumably alpha amylase inhibitor, bands as illustrated in FIG. 2. According to the LC-MS/MS data obtained from the extracted proteins, the most abundant proteins present in bands C1 and B1 are wheat alpha amylase inhibitors with the SwissProt accession numbers P17314 (CM 3) and P16159 (CM 16), in bands E1 and D1 the wheat alpha amylase inhibitors P01085 (0.19), P16851 (CM 2) and P16159 (CM 16) and in bands G1 and F1 P01083 (CM 3).

This data demonstrates that the *Aspergillus niger* aspergilloglutamic peptidase is surprisingly the most efficacious in degrading wheat derived alpha amylase inhibitors under stomach conditions and most notably, wheat alpha amylase inhibitors: CM 2, CM 3, CM 16, and 0.19.

Example 2: *Aspergillus niger* Aspergilloglutamic Peptidase Cleaves Alpha Amylase/Trypsin Inhibitors in Beer and Stabilizes Foam According to their amino acid sequences, barley incorporates alpha amylase inhibitors that are very similar to alpha amylase inhibitors present in wheat. Therefore, beer presents a food product that could be relevant for gluten sensitive individuals. In beer, as in other food products, the alpha amylase inhibitors are present either as an intact molecule or as peptides large enough to elicit an immune response. For example, in an LC-MS/MS analysis of 16 different beers, we identified about 3300 different peptides larger than 9 amino acids with sequences attributed to alpha amylase inhibitors. This finding illustrates the potential relevance of alpha amylase inhibitors for gluten sensitive individuals and thereby the relevance of the aspergilloglutamic peptidase for beer production.

The use of proteases during the beer fermentation phase or beyond is quite common for preventing the so called chill haze. Historically acid proteases with a broad specificity like Proctase or papain were used for this purpose, but nowadays a proline-specific endoprotease called Brewers Clarex presents the preferred option. The main reason for shifting from such broad specificity enzymes towards the highly specific Brewers Clarex product is that application of the broad specificity enzymes tends to result in beers with a poor foaming capacity. So any negative impact on beer foam is a prerequisite for the acceptability of a proteolytic treatment during beer production. To test the effect of the *Aspergillus niger* aspergilloglutamic peptidase on beer foam formation, the following experiment was carried out.

Bottled beers of a large, international brand were obtained from a local supermarket. The bottles were carefully opened, the relevant enzyme(s) were added and immediately the bottles were closed again using a new crown cork. After careful mixing, the bottles were stored at 20 degrees ° C. The data presented in Example 1 above, show that the concentration of aspergilloglutamic peptidase required to destroy alpha amylase inhibitors is at least ten times lower than the concentration of the proline specific endoprotease. The typical industrial use level of the commercial proline-specific Brewers Clarex product is 3 grams/hi beer which corresponds with 150 mg of pure enzyme protein per hl of beer. In the present experiment, the proline specific endoprotease was also added in this concentration, but the other two proteases were added in concentrations of only 15 mg of pure enzyme protein per hl of beer. After incubation for one week, the foam stability of all beers was measured according to the Analytica-EBC method 9.42 using Haffmans equipment (Inpack 2000 Sampler in combination with the Foam Stability Tester Nibem TPH, Haffmans BV, Venlo, The Netherlands). The average foam values of two duplicates per incubation are shown in Table 1.

As expected, the foam stability of the beers incubated with the proline-specific endoprotease added in concentrations suitable for chill haze prevention (i.e. 150 mg/hl) are comparable with the data obtained for the reference product (commercial beer without protease added). The surprising observation is that upon the addition of a low concentration of the aspergilloglutamic peptidase or of an aspergillopepsin I-like enzyme, the stability of the beer foam is significantly increased, even if it is applied in combination with industrially used levels of the proline-specific endoprotease. This result suggests that addition of the aspergilloglutamic peptidase, for example with the intention to destroy large peptides of alpha amylase inhibitors, has beer foam stabilization as a desirable side effect.

TABLE 1

Foam stability of beer incubated with various enzymes

| Enzyme(s) added | Foam (seconds) |
|---|---|
| Reference | 252 |
| Proline-specific endoprotease (150 mg/hl) | 250 |
| Proline-specific endoprotease (15 mg/hl) | 252 |
| Aspergilloglutamic peptidase (15 mg/hl) | 280 |
| Multifect 15 L (15 mg/hl) | 255 |

Example 3: *Aspergillus niger* Aspergilloglutamic Peptidase Cleaves Alpha Amylase/Trypsin Inhibitors in a Dose Dependent Manner In the present Example we determine the quantity of *A. niger* aspergilloglutamic peptidase enzyme protein required to hydrolyze under simulated stomach conditions the alpha amylase/protease inhibitors present in 1 gram of wheat gluten. To that end gluten from wheat (Sigma) was solubilized in 50 mmol/l citric acid pH 4.0 in a concentration of 9.35 mg/ml. To this thoroughly stirred mixture pepsin enzyme protein was added to reach an end concentration of 0.2 mg/ml and then six one ml samples were taken. To these six samples increasing quantities of pure *A. niger* aspergilloglutamic peptidase enzyme were added. To sample 1: no AGP was added, to sample 2: 0.09 mg, to sample 3: 0.19 mg, to sample 4: 0.28 mg, to sample 5: 0.37 mg and to the last sample: 0.47 mg. The different samples were than incubated for 60 minutes at 37 degrees Celcius and from each sample aliquots for SDS-PAGE analysis were taken at t=0 minutes and t=60 minutes. SDS-PAGE analysis was carried out according to the Invitrogen protocol.

Figure 3:
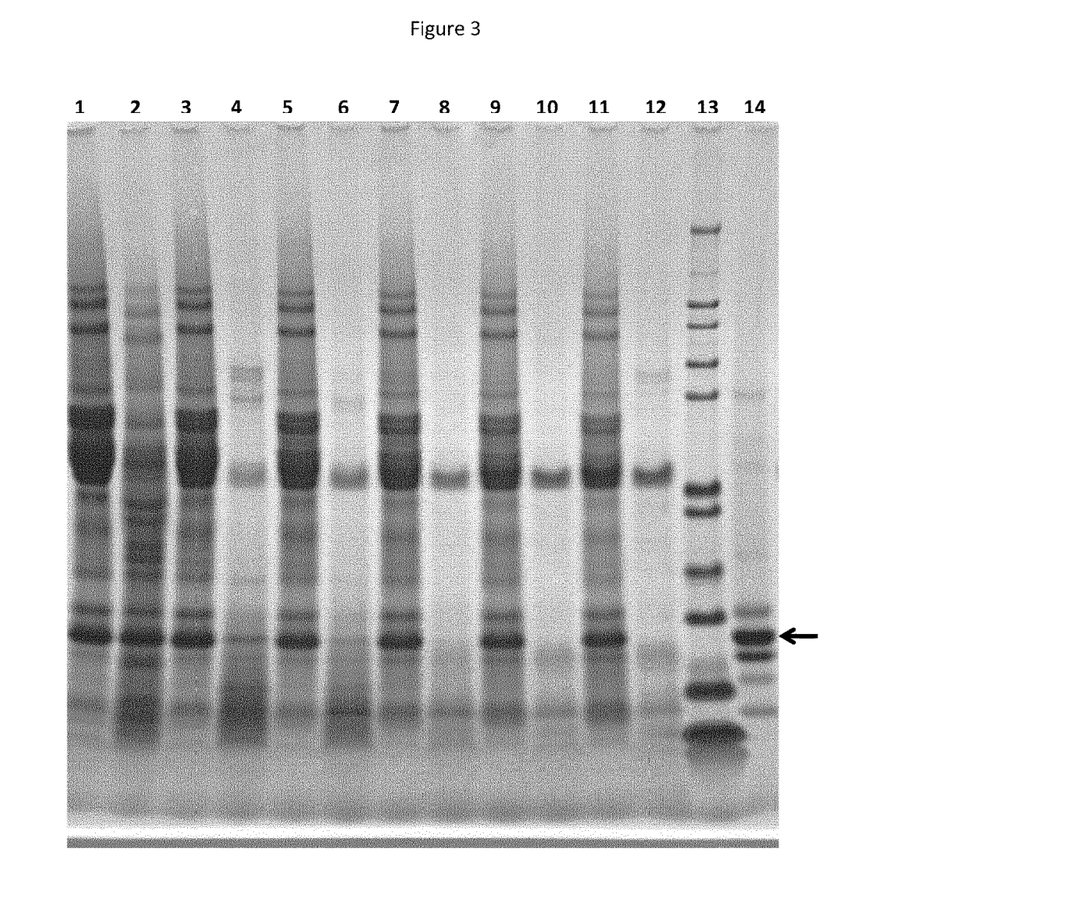
FIG. 3: 4-12% SDS-PAGE (4 to 12% Bis-Tris gel) analysis of various incubations of a standardized quantity of wheat gluten with increasing *A. niger* aspergilloglutamic peptidase (AGP) concentrations under simulated stomach conditions. The arrow indicates the position of the wheat alpha amylase inhibitors 0.19, CM2 and CM16 (see Example 1).

The results (cf. FIG. 3) show that by adding 0.28 mg of pure *A. niger* aspergilloglutamic peptidase the alpha amylase/protease inhibitors present in 9.35 mg of wheat gluten can be hydrolyzed within a one hour period. This implies that 30 mg of pure *A. niger* aspergilloglutamic peptidase (corresponding with 15 000 HPU) can cope with 1 gram of wheat gluten under such simulated gastric conditions. Thus, after the partial fragmentation of alpha amylase/protease inhibitors by an oral *A. niger* aspergilloglutamic peptidase preparation, the newly generated inhibitor peptides will be further degraded to non-immunogenic oligo-peptides by pepsin during stomach passage and, after entering the duodenum, by pancreatic proteases such as trypsin and chymotrypsin.

Example 4: The Aspergillopepsin I Homologue from *T. reesei* can Cleave Wheat Derived Purothionins Under Gastric Conditions Materials & Methods Purothionins were isolated as described by Ohtani et al (J. Biochem. 82, 753-767 (1977)) with some modifications. Wheat supernatant was chromatographed on SP Sepharose 6 FF (Amersham) equilibrated with 20 millimol/l sodium phosphate, pH 7.2 and eluted with a linear gradient of 0 to 1.0 mol/l NaCl in the same buffer. The presence of pure purothionin with a molecular weight of approximately 5 kDa in the various fractions was followed by SDS-PAGE. The fractions showing a single protein band were pooled, concentrated using an Amicon 3 kDa membrane and then freeze dried. The identity and the purity of the protein isolated was confirmed by LC-MS/MS analysis essentially as described in Example 1 using the Uniprot/Swissprot database.

Enzymatic Assay

Incubations of the purified purothionins with the various proteases were carried out in 50 mmol/l Na citrate at pH 4.0 for 90 minutes at 37° C., similar to the conditions specified in Example 1 of the present application. In all relevant incubations pepsin was present in an enzyme protein concentration of 0.2 mg/ml. The aspergilloglutamic peptidase, the proline-specific endoproteinase and the Multifect PR 15 L were tested in a concentration of 0.11 mg enzyme protein/ml. The wheat purothionine was added last and was present in a concentration of 0.44 mg/ml.

Results

In the experiment the efficacies of the following enzymes were compared in the presence of pepsin:

*Aspergillus niger* aspergilloglutamic peptidase also called aspergillopepsin II (MaxiPro HSP, DSM Food Specialities, Delft, The Netherlands), proline-specific endoproteinase from *Aspergillus niger* (MaxiPro PSP, DSM Food Specialities, Delft, The Netherlands)

Multifect PR 15 L (aspergillopepsin I-like protease from *Trichoderma reesei*; http//biosciences.dupont.com).

Figure 4:
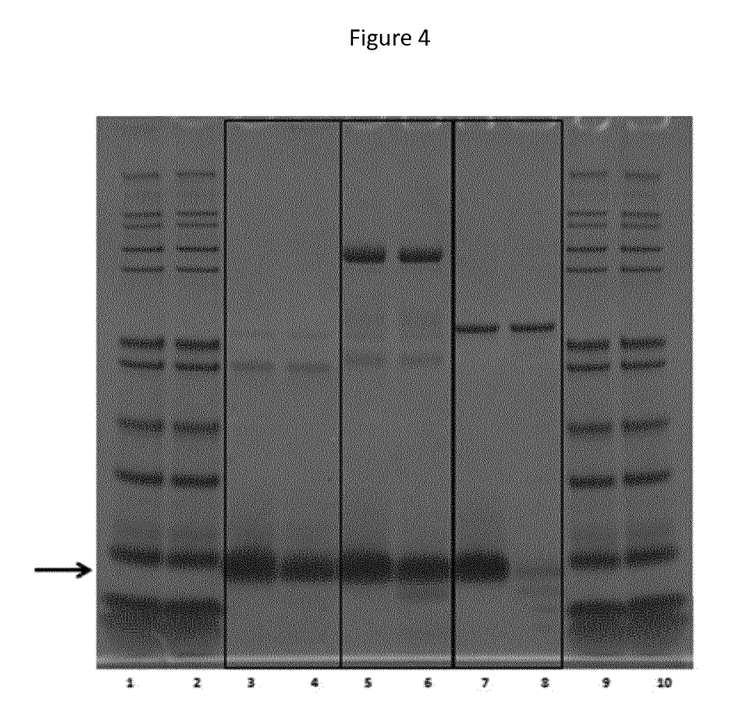
FIG. 4: 4-12% SDS-PAGE (4 to 12% Bis-Tris gel) analysis of various incubations of wheat derived purothionins with different proteases plus pepsin under simulated stomach conditions. The arrow indicates the position of the purified purothionins.

The results obtained (cf. FIG. 4) show that under simulated stomach conditions and equal amounts of the various proteinases, the aspergillopepsin I-like protease from *Trichoderma reesei* effectively degrades wheat derived purothionine.

Example 5: Cleavage of Wheat Derived Purothionins Under Gastric Conditions

Materials & Methods

Purothionins were isolated from wheat as described in Example 4. Proctase was obtained from Meiji (Tokyo, Japan).

Results

Figure 5:
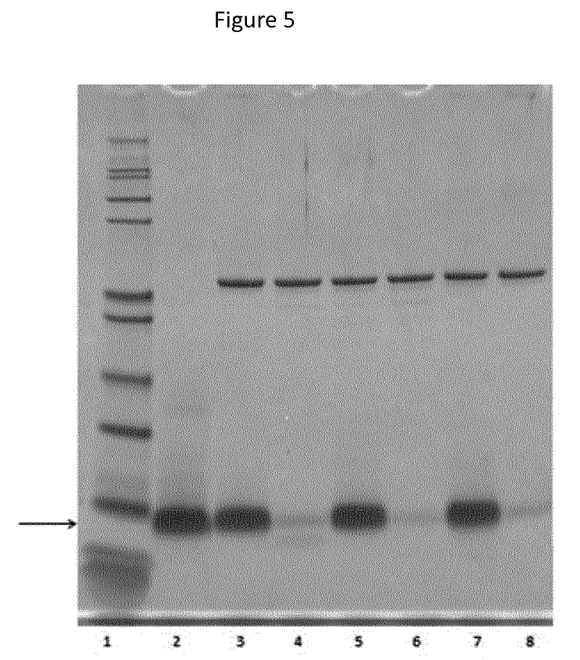
FIG. 5: 4-12% SDS-PAGE (4 to 12% Bis-Tris gel) analysis of various incubations of wheat derived purothionins with different proteases plus pepsin under simulated stomach conditions. The arrow indicates the position of the purified purothionins.

As illustrated by the digestion products of wheat purothionins in FIG. 5, enzyme products incorporating either aspergillopepsin I from *Aspergillus niger* or its homologue from *Trichoderma reesei* can hydrolyze wheat purothionins under simulated stomach conditions.

Example 6: At their Effective Dosages, Aspergilloglutamic Peptidase and Aspergillopepsin I-Like Enzymes have No Detrimental Effect on Beer Foam Beer incorporates the barley derived alpha-amylase/trypsin inhibitors that are known to be highly homologous to the allergenic alpha-amylase/trypsin inhibitors present in wheat (Okada et al., J. Agric. Food Chem. 2008, 56, 1458-1464). The results shown in Example 1 of the present application show that aspergilloglutamic peptidase can effectively hydrolyze various alpha-amylase/trypsin inhibitors. Therefore, upon addition of the aspergilloglutamic peptidase to beer, it can be expected that also the alpha-amylase/trypsin inhibitors from barley are hydrolyzed. In Example 2 we show that adding the relevant acid proteases have no negative effect on the quality of beer foam. In the present Example we show that enzyme dosages of the aspergilloglutamic peptidase, the aspergillopepsin I and the aspergillopepsin I homologue of *Trichoderma reesei* required to hydrolyse known beer allergens like the alpha-amylase/trypsin inhibitors and Protein Z (Garcia-Casado et al., J Allergy Clin Immunol, 108(4), pp 647-649) have no detrimental effects on beer foam stability, not even in combination with the quantities of proline-specific endoprotease (MaxiPro PSP, DSM Food Specialities, Delft, The Netherlands) required to prevent chill haze.

Bottled beers of a large, international brand were obtained from a local supermarket. The bottles were carefully opened, the relevant enzymes were added and immediately the bottles were closed again using a new crown cork. After careful mixing, the bottles were stored at 20 degrees C. for one week. Foam stabilities were measured as described in Example 2 and the average foam values of two duplicates per incubation are shown in Table 2. The data obtained clearly demonstrate that the high dosages of the various acid proteases added have no detrimental effect on the foams formed.

TABLE 2

Foam stability of beer incubated with various proteolytic enzymes

| Enzymes added | Foam [seconds] |
|---|---|
| Proline-specific endoprotease 150 mg/hl | 250 |
| Proline-specific endoprotease 50 mg /hl | 247 |
| Proline-specific endoprotease 15 mg/hl | 259 |
| Aspergilloglutamic protease 150 mg/hl | 268 |
| Aspergilloglutamic protease 50 mg/hl | 273 |
| Aspergilloglutamic protease 15 mg/hl | 280 |
| Multifect PR15L 150 mg/hl | 270 |
| Multifect PR15L 50 mg/hl | 276 |
| Multifect PR15L 15 mg/hl | 255 |
| Aspergillopepsin I 150 mg/hl | 284 |
| Aspergillopepsin I 50 mg/hl | 267 |
| Aspergillopepsin I 15 mg/hl | 266 |
| Proline-specific endoprotease 150 mg/hl + Aspergiilopepsin I 15 mg/hl | 264 |
| Proline-specific endoprotease 150 mg/hl + Multrfect PR 15 L 15 mg/hl | 266 |
| Proline-specific endoprotease 150 mg/hl + Aspergillopepsin I 15 mg/hl | 265 |
| Reference beer | 252 |
| Reference beer + 0.75 ml H2O | 259 |

The invention claimed is:

1. A dietary supplement or a pharmaceutical composition comprising an *Aspergillus niger* aspergilloglutamic peptidase, a prolyl-endopeptidase which is *Aspergillus niger* prolylendopeptidase enzyme (AN-PEP), and pharmaceutically or dietary acceptable excipients.

2. A dietary supplement or a pharmaceutical composition according to claim 1, further comprising an aspergillopepsin I.

3. A dietary supplement or a pharmaceutical composition according to claim 1, wherein the supplement is in the form of a tablet, capsule or a liquid formulation.

4. A method of treating a patient suffering from innate immune response in the intestine, comprising administering to the patient an effective amount of the dietary supplement or pharmaceutical composition of claim 1.

5. The method of claim 4, wherein the composition further comprises an aspergillopepsin I.

6. A method of treating a patient suffering from celiac disease, non-celiac gluten intolerance, gluten sensitivity, irritable bowel syndrome, or inflammatory bowel disease, comprising administering to the patient an effective amount of the dietary supplement or pharmaceutical composition of claim 1.

7. A method for maintaining or enhancing gastrointestinal comfort in gluten sensitive individuals, for delaying the onset of gastrointestinal discomfort in celiac or non-celiac gluten sensitive individuals, or for decreasing alpha-amylase/trypsin inhibitor exposure in healthy individuals, comprising administering to an individual in need thereof an effective amount of the dietary supplement or pharmaceutical composition of claim 1.

8. The method of claim 4, wherein the composition is administered orally within 1 hour prior or after a meal.

9. The method of claim 6, wherein the composition further comprises an aspergillopepsin I.

10. The method of claim 6, wherein the composition is administered orally within 1 hour prior or after a meal.

11. The method of claim 7, wherein the composition further comprises an aspergillopepsin I.

12. The method of claim 7, wherein the composition is administered orally within 1 hour prior or after a meal.

\* \* \* \* \*